United States Patent
Ottow et al.

(10) Patent No.: US 6,996,479 B2
(45) Date of Patent: Feb. 7, 2006

(54) METHOD AND APPARATUS FOR MEASURING AND CONTROLLING THE WATER CONTENT OF A WATER-CONTAINING LIQUID MIXTURE

(75) Inventors: Stefan Ottow, Dresden (DE); Martin Welzel, Dresden (DE); Dan Wissel, Austin, TX (US)

(73) Assignees: Infineon Technologies AG, Munich (DE); Motorola Inc., Schaumburg, IL (US); Infineon Technologies SC300 GmbH & Co., KG, Dresden (DE)

( * ) Notice: Subject to any disclaimer, the term of this patent is extended or adjusted under 35 U.S.C. 154(b) by 235 days.

(21) Appl. No.: 10/403,878

(22) Filed: Mar. 31, 2003

(65) Prior Publication Data

US 2003/0176979 A1 Sep. 18, 2003

Related U.S. Application Data

(63) Continuation of application No. PCT/EP01/10188, filed on Sep. 4, 2001.

(30) Foreign Application Priority Data

Sep. 29, 2000 (EP) .............................................. 00121486

(51) Int. Cl.
*G06F 19/00* (2006.01)

(52) U.S. Cl. .......................... 702/25; 702/130; 702/136; 702/138; 702/182; 134/19; 134/107; 134/108

(58) Field of Classification Search ................... 702/25, 702/130, 136, 138, 182; 134/19, 107, 108, 134/109, 902; 122/14.22, 18.1, 367.1, 448.1; 210/634, 640, 651
See application file for complete search history.

(56) References Cited

U.S. PATENT DOCUMENTS

| | | | |
|---|---|---|---|
| 4,766,553 A | | 8/1988 | Kaya et al. |
| 4,852,524 A | * | 8/1989 | Cohen ...................... 122/448.1 |

(Continued)

FOREIGN PATENT DOCUMENTS

| DE | 195 48 115 A1 | 7/1996 |
|---|---|---|
| EP | 0 474 482 A1 | 3/1992 |

(Continued)

OTHER PUBLICATIONS

Van Gelder, W. et al.: "The Etching of Silicon Nitride in Phosphoric Acid with Silicon Dioxide as a Mask", Journal Electrochemical Society, vol. 144, No. 8, Aug. 1967, pp. 869–872.

*Primary Examiner*—Carol S. W. Tsai
(74) *Attorney, Agent, or Firm*—Laurence A. Greenberg; Werner H. Stemer; Ralph E. Locher

(57) ABSTRACT

An apparatus for measuring the water content of a water-containing liquid mixture contained in a tight chemistry tank includes a heating device for controlling the temperature of the liquid mixture to a temperature near the boiling point of the liquid mixture, a cooling medium system disposed at the top of the tight chemistry tank having a cooling medium inlet and a cooling medium outlet, a temperature measurement system for determining the temperature difference between the cooling medium inlet and outlet, and a computing device for calculating the water content of the liquid mixture from the temperature difference. Also provided is a tank for supplying water to the liquid mixture, and a control system for adjusting the amount of water supplied from the tank based upon the water content measured by the measuring apparatus. Also provided is a method for measure the water content.

26 Claims, 2 Drawing Sheets

U.S. PATENT DOCUMENTS

| | | | |
|---|---|---|---|
| 5,078,832 A | * 1/1992 | Tanaka | 216/94 |
| 5,143,103 A | * 9/1992 | Basso et al. | 134/98.1 |
| 5,151,190 A | * 9/1992 | Seiryo | 210/640 |
| 5,213,725 A | * 5/1993 | Lee et al. | 264/37.16 |
| 5,365,960 A | * 11/1994 | Bran | 134/184 |
| 5,390,632 A | * 2/1995 | Ikebe et al. | 123/41.02 |
| 5,585,729 A | 12/1996 | Toshima et al. | |
| 5,681,448 A | 10/1997 | Uchiyama et al. | |
| 5,779,927 A | 7/1998 | Lo | |
| 5,782,080 A | * 7/1998 | Illbruck | 60/39.59 |
| 5,938,885 A | 8/1999 | Huang et al. | |
| 6,110,274 A | * 8/2000 | Okuno | 117/81 |
| 6,152,209 A | * 11/2000 | Pleschiutschnigg | 164/455 |
| 6,221,167 B1 | * 4/2001 | Karasawa | 134/1 |
| 6,445,880 B1 | * 9/2002 | Hollander et al. | 392/485 |
| 6,463,748 B1 | * 10/2002 | Benedict et al. | 62/228.1 |
| 6,470,144 B1 | * 10/2002 | Tarutani et al. | 392/396 |
| 6,678,628 B2 | * 1/2004 | Ryan et al. | 702/132 |

FOREIGN PATENT DOCUMENTS

| | | |
|---|---|---|
| EP | 0 508 212 A1 | 10/1992 |
| EP | 0 703 604 B1 | 3/1996 |
| JP | 62-272542 | 11/1987 |
| JP | 08296797 A * | 11/1996 |

* cited by examiner

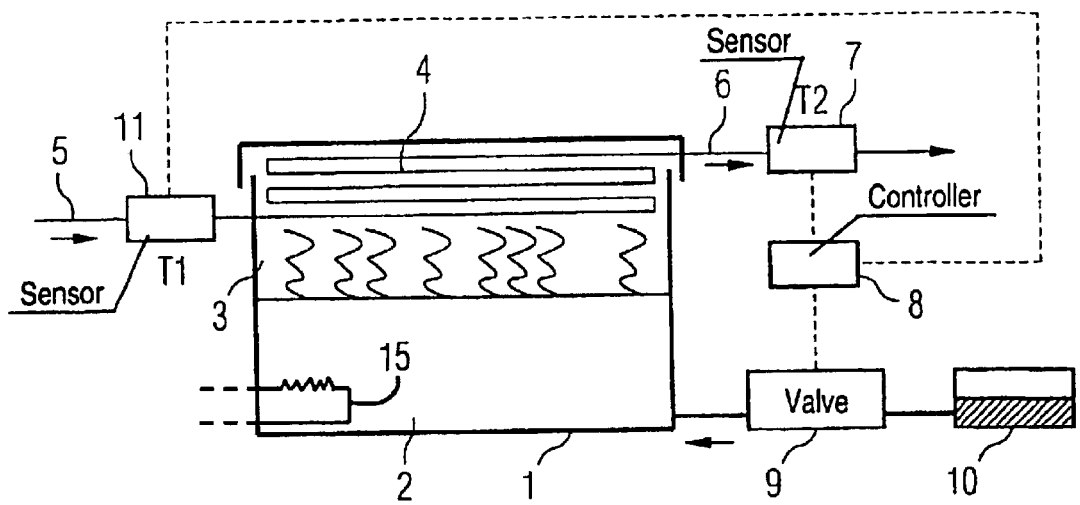
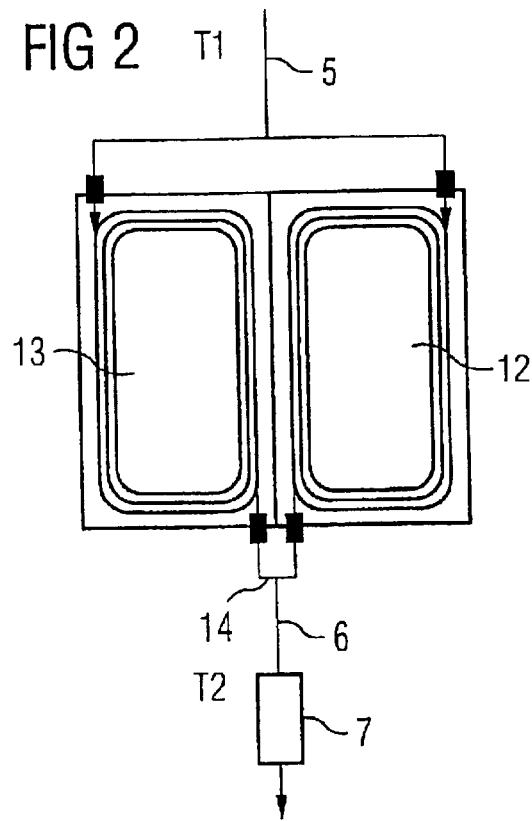

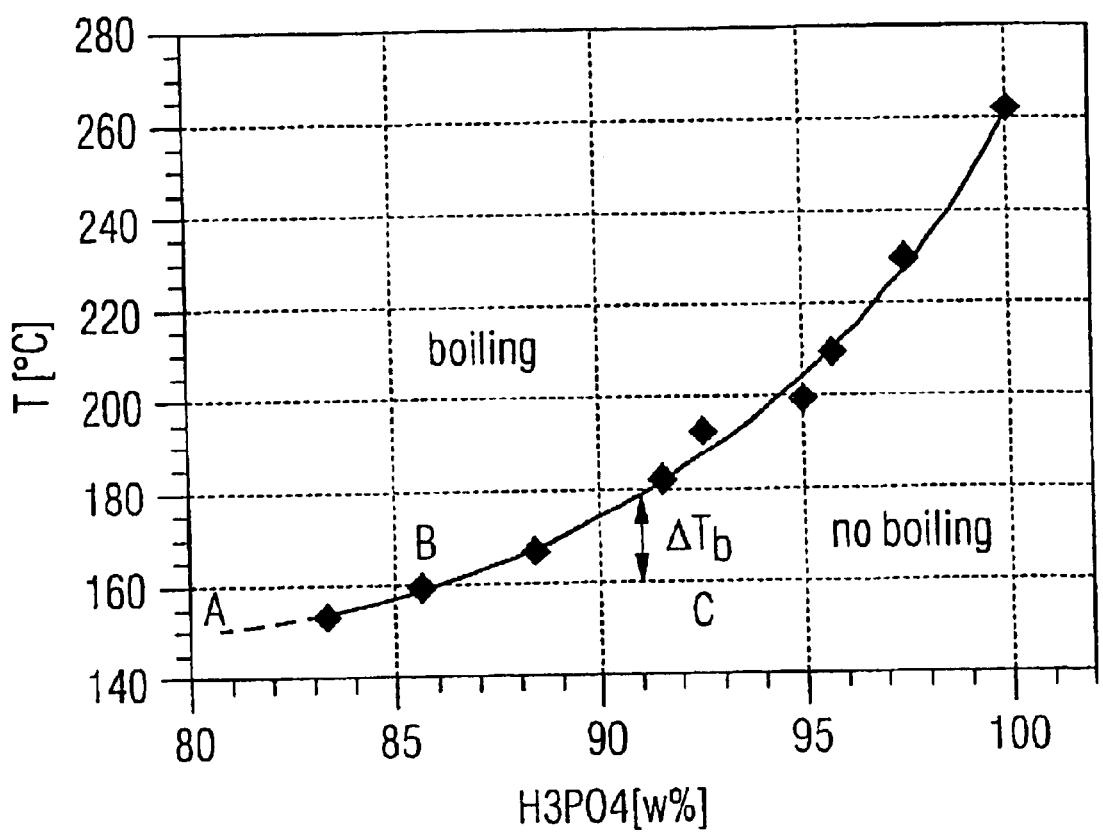

METHOD AND APPARATUS FOR MEASURING AND CONTROLLING THE WATER CONTENT OF A WATER-CONTAINING LIQUID MIXTURE

CROSS-REFERENCE TO RELATED APPLICATION

This application is a continuation of copending International Application No. PCT/EP01/10188, filed Sep. 4, 2001, which designated the United States.

BACKGROUND OF THE INVENTION

Field of the Invention

The present invention generally relates to an apparatus and a method for measuring as well as controlling the water content of water-containing liquid mixture contained in a tank.

In particular, the present invention relates to an apparatus and a method for the in-situ control of the water content in a so-called hot phosphoric acid (HOT PHOS) baths.

Usually, in the manufacture of semiconductor integrated circuits, HOT PHOS baths are used for wet-etching of silicon nitride. Silicon nitride is generally used as a masking layer. When it becomes necessary to remove the silicon nitride mask, normally, wet etching with hot phosphoric acid at 160° C. with approximately 85 wt-% $H_3PO_4$ is used.

$$Si_3N_4 + 6H_2O \xrightarrow{H_3PO_4} 3SiO_2 + 4NH_3 \quad \text{(Equation 1)}$$

Because the etching rate of silicon nitride is more than ten times higher than the etching rate of silicon dioxide, silicon nitride is selectively etched. However, two important factors influence the etching rate of both silicon nitride and silicon dioxide: 1) the bath temperature that is normally a constant temperature at around 160° C., and 2) the water content of the bath.

The water content of the bath varies because of the continuous water evaporation due to the high temperature, the water evaporation during lid opening, and the chemical reaction as indicated above. So far, a constant amount of water is continuously spiked during the process, but such a procedure is not well controlled and the amount of spiked water is often determined empirically.

To maintain constant the water content in a phosphoric acid/water system used for silicon nitride etching, U.S. Pat. No. 5,779,927 to Lo suggests an apparatus and a method in which the liquid acid evaporant is condensed and returned to the main volume of the acid. To control the amount of pure water added, either the pH of the condensed evaporant is measured or, alternatively, the conductivity of the phosphoric acid/water system is measured.

However, these measurement mechanisms involve major structural changes of the etching apparatus. In particular, a special piping has to be attached to the apparatus to return the condensate through the pH meter to the acid bearing container.

SUMMARY OF THE INVENTION

It is accordingly an object of the invention to provide a method and apparatus for measuring and controlling the water content of a water-containing liquid mixture that overcomes the hereinafore-mentioned disadvantages of the heretofore-known devices and methods of this general type and that provides an improved apparatus and an improved method for the in-situ measurement of the water content of a hot liquid mixture that contains water and for the in-situ control of the water content of a hot liquid mixture that contains water.

With the foregoing and other objects in view, there is provided, in accordance with the invention, an apparatus for measuring the water content of a water-containing liquid mixture contained in a tank, the water-containing liquid mixture having a boiling point, the apparatus including a heating device for controlling temperature of the liquid mixture to a temperature near the boiling point of the liquid mixture, a cooling medium system having a cooling medium inlet and a cooling medium outlet, the cooling medium system being disposed at a top of the tank and conveying a cooling medium, a temperature measurement system connected to the cooling medium system for determining a temperature difference between the cooling medium inlet and the cooling medium outlet, and a computing device connected to the temperature measurement system for calculating the water content of the liquid mixture from the temperature difference.

With the objects of the invention in view, there is also provided an apparatus for measuring the water content of a water-containing liquid mixture, including a tank for holding a water-containing liquid mixture having a boiling point, the tank having a top, a heating device at the tank for controlling temperature of the liquid mixture to a temperature near the boiling point of the liquid mixture, a cooling medium system having a cooling medium inlet and a cooling medium outlet, the cooling medium system being disposed at the top of the tank and conveying a cooling medium, a temperature measurement system connected to the cooling medium system for determining a temperature difference between the cooling medium inlet and the cooling medium outlet, and a computing device connected to the temperature measurement system for calculating the water content of the liquid mixture from the temperature difference.

In accordance with another feature of the invention, there is provided a tank for supplying water to the liquid mixture, and a control system for adjusting the amount of water supplied from the tank based upon the water content measured by the apparatus for measuring the water content.

With the objects of the invention in view, there is also provided a method for measuring the water content of a water-containing liquid mixture contained in a tank with a cooling medium system disposed at the top of the tight chemistry tank, the cooling medium system having a cooling medium inlet and a cooling medium outlet, including the steps of controlling the temperature of the liquid mixture to a temperature near the transition point of the liquid mixture, determining the temperature difference between cooling medium inlet and cooling medium outlet, and calculating the water content of the liquid mixture from the temperature difference.

With the objects of the invention in view, there is also provided a method for measuring water content of a water-containing liquid mixture having a boiling point, including the steps of disposing a cooling medium system at a top of a tank containing the liquid mixture, the cooling medium system having a cooling medium inlet and a cooling medium outlet, controlling a temperature of the liquid mixture to a temperature near the boiling point of the liquid mixture, determining a temperature difference between the cooling medium inlet and the cooling medium outlet, and calculating the water content of the liquid mixture from the temperature difference.

In accordance with a further mode of the invention, there is provided the step of adjusting the amount of water supplied from a water supply tank based upon the measured water content.

In accordance with an additional feature of the invention, the cooling medium inlet is held at a constant temperature.

In accordance with yet another feature of the invention, the computing device is connected to the cooling medium inlet and holds the cooling medium inlet at a constant temperature.

In accordance with yet a further feature of the invention, the cooling medium system is divided into at least two symmetrical branches each having at least one loop.

In accordance with an added feature of the invention, the temperature of the liquid mixture is, preferably, to be held constant.

The measurement principle underlying the present invention will be described with reference to a phosphoric acid/water system that is the water-containing liquid mixture in the embodiment. However, the described apparatus and method can also be used with any other liquid mixture that contains water, which is held at a temperature near the boiling point of the liquid mixture.

As can be seen from FIG. 3, the boiling point of phosphoric acid depends on the phosphoric acid concentration. FIG. 3, which is taken from W. van Gelder, V. E. Hauser, J. Electrochem Soc., 114, 869 (1967), illustrates the dependence of the boiling point of phosphoric acid on the phosphoric acid concentration at a pressure of $1.013*10^5$ Pa.

The amount of evaporated water of a mixture at a constant temperature depends only on the concentration of water in the liquid mixture.

In accordance with yet an added feature of the invention, the cooling medium is water.

In accordance with yet an additional feature of the invention, the tank has a lid and the cooling medium system is housed in the lid.

This water can be condensed back on cooling lids or a condensation line in general on top of the process tank, respectively. Because the lids are water cooled, the condensation is accelerated. The tank is, preferably, a tight chemistry tank. However, as the system is not a closed system, there is a continuous loss of evaporated water. Besides this, water is also consumed by the reaction described in Equation 1.

The basic idea underlying the present invention is to measure the temperature difference induced by the condensation rate $\Delta T(cr)$ between cooling water let in and out of the condensation line. At a constant flow and a constant temperature of the cooling medium, the temperature difference between inlet and outlet of the cooling lines is dependent on the condensation rate:

$$\Delta T(cr)=T_2(cr)-T_1, \quad \text{(Equation 2)}$$

where $T_2(cr)$ denotes the temperature of the cooling medium outlet, and $T_1$ denotes the temperature of the cooling medium inlet.

The temperature difference $\Delta T(cr)$ is proportional to the amount of evaporated water $mH_2O_{evap}$. The amount of evaporated water is inversely proportional to $\Delta T_b$. As shown in FIG. 3, $\Delta T_b$ is the difference between the controlled temperature of the current liquid mixture and the boiling point of the mixture at this concentration, therefore:

$$\Delta T(cr) \sim mH_2O_{evap} \sim 1/\Delta T_b. \quad \text{(Equation 3)}$$

In other words, $\Delta Tb$ is inversely proportional to the water concentration in the bath, therefore:

$$\Delta Tb \sim 1/[H_2O_{bath}]. \quad \text{(Equation 4)}$$

Accordingly, the following relation holds:

$$\Delta T(cr) \sim [H_2O_{bath}]. \quad \text{(Equation 5)}$$

For the purpose of the present invention, it is required that both the bath temperature and the cooling medium inlet temperature are maintained constant or at least temperature controlled allowing for temperature compensation. Moreover, the bath is held at a constant temperature near the boiling point of the liquid mixture, i.e., the boiling temperature ±5%.

This temperature difference signal of the cooling water system is fed to a computing device for calculating the water content of the aqueous solution. The computing device uses appropriate software that is able to compensate for temperature differences, for instance, when a lot is going into the process tank and the lids are open for a certain time.

The signal representing the calculated water content can be used to adjust the correct water spiking rate.

In summary, the apparatus and methods of the present invention provide the following advantages:

The apparatus and methods of the present invention allow an in-situ control of the water content in HOT PHOS baths. Accordingly, the etching rate can exactly be adjusted and stabilized. Moreover, the lifetime of the bath and the quartz tank can be extended;

The apparatus and method of the present invention can easily be installed. Only a temperature measurement system and a computing device, as well as a control system for adjusting the amount of water supplied, have to be attached to the normally used etching reactor. Accordingly, no significant hardware changes are necessary; and The apparatus and method of the present invention can easily be adapted to other spiking processes with condensation lines, the spiking processes running at a constant temperature.

The cooling medium used for the present invention can be any suitable cooling medium, for example, water, an appropriate fluid, or gas.

According to the present invention, the cooling medium system is disposed at the top of the process tank. According to an embodiment of the present invention, the cooling medium is housed in the lid of the process tank. In particular, the cooling medium can be implemented as a cooling coil including one or more loops to increase the condensing surface.

The invention increases the bath lifetime because the concentration of the HOT PHOS bath is held within the optimum range. Further, product quality is increased by maintaining a constant etch rate over the bath lifetime.

Other features that are considered as characteristic for the invention are set forth in the appended claims.

Although the invention is illustrated and described herein as embodied in a method and apparatus for measuring and controlling the water content of a water-containing liquid mixture, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

FIG. 1 is a side view of an apparatus according to the invention;

FIG. 2 is a plan view of an cooling medium system according to the invention; and FIG. 3 is a graph illustrating a dependence of the boiling point of phosphoric acid on the concentration of phosphoric acid.

DESCRIPTION OF THE PREFERRED EMBODIMENTS

Referring now to the figures of the drawings in detail and first, particularly to FIG. 1 thereof, there is shown a process tank 1 housing the HOT PHOS bath 2 that, in the present case, is an approx. 86% $H_3PO_4$ under well controlled processing conditions. During the etching process, for example, non-illustrated silicon wafers partially coated with a silicon nitride layer, are immersed into the HOT PHOS bath 2. Reference numeral 3 denotes the water evaporated from the HOT PHOS bath. A heating device 15, for instance, inline heaters, are provided to hold the HOT PHOS bath 2 at a constant temperature, which is, in the present case, near 160° C. The pressure inside the process tank 1 is at normal air pressure.

The process tank 1 is lid cooled by the cooling water system 4 having a cooling water inlet 5 and a cooling water outlet 6. The cooling water inlet 5 is held at a constant temperature $T_1$ which temperature is measured by a temperature sensor 11, and the temperature $T_2$ of the cooling water outlet 6 is measured by a temperature sensor 7. Non-illustrated control measures are provided to maintain a constant flow of the cooling water across the cooling water system so that the heat is uniformly carried off. A controller or computer 8 calculates the temperature difference between the outlet temperature T2 and the inlet temperature T1. The controller acts to hold the temperature constant in the steady state. In addition a non-illustrated flow meter can be inserted at the inlet 5. The flow meter provides a signal to the controller 8 so that the system can process the amount of liquid flow.

As shown in FIG. 2, the cooling water system can be divided into two symmetrical branches including a right lid 12 and a left lid 13. Each of the two branches is implemented as a cooling loop including one or more loops. The two symmetrical branches are joined at a junction point 14, and the temperature of the joined branches is measured by the temperature sensor 7. Of course, the cooling water system can also be divided into more than two symmetrical branches.

As can be seen from FIG. 1, the temperature difference between cooling water inlet and outlet is given to the controller 8, which is provided with appropriate software so that the water content of the HOT PHOS bath can be determined from the temperature difference.

A signal provided by the controller 8 is given to the valve 9 or a spiking pump that controls the water amount supplied by the water tank 10.

In the course of time, the water content of the HOT PHOS bath 2 will vary. In case the HOT PHOS concentration increases, less $H_2O$ will be evaporated. Consequently, the temperature difference between cooling water outlet and cooling water inlet will decrease, and the water spiking has to be increased. In case the HOT PHOS concentration decreases, more $H_2O$ will be evaporated. Consequently, the temperature difference between cooling water outlet and cooling water inlet will increase, and the water spiking has to be decreased.

Referring to FIG. 3, the dashed line represents the different possible states in the bath. Starting for instance, at a $H_3PO_4$ concentration of approximately 81 wt-% (marked as A) the desired temperature of 160° C. cannot be reached until the water concentration is reduced by boiling to the relating point of B.

Van Gelder and Hauser, J. Electrochem. Sec., 114, 869 (1967) reported that the vapor phase in equilibrium with phosphoric acid is virtually pure water up to temperatures of 250° C. Assuming a bath at a constant temperature of 160° C. without spiking possibility, mainly, the water concentration is permanently decreased in direction to reference point C due to the fact that the system is an open system.

In case of water spiking, the concentration of water is held nearly constant and the state in the bath is always between B and C close to point B. As mentioned above, $\Delta T_b$ is the temperature difference between the controlled temperature of the current liquid mixture and the boiling point of the mixture at a given concentration between B and C.

We claim:

1. An apparatus for measuring the water content of a water-containing liquid mixture contained in a tank, the water-containing liquid mixture having a boiling point, the apparatus comprising:

a tank for holding the water-containing liquid mixture, said tank having a top;

a heating device for controlling temperature of the liquid mixture to a temperature near the boiling point of the liquid mixture;

a cooling medium system for cooling the liquid mixture, said cooling medium system having:

a condensing surface to condense water evaporating from the liquid mixture in said tank; and a cooling medium inlet and a cooling medium outlet, said cooling medium system being disposed at said top of said tank and conveying a cooling medium;

a temperature measurement system connected to said cooling medium system for determining a temperature difference between said cooling medium inlet and said cooling medium outlet; and a computing device connected to said temperature measurement system for calculating the water content of the liquid mixture from said temperature difference.

2. The apparatus according to claim 1, wherein the liquid mixture is an acid/water system.

3. The apparatus according to claim 2, wherein the acid of the acid/water system is phosphoric acid.

4. The apparatus according to claim 1, wherein said cooling medium inlet is held at a constant temperature.

5. The apparatus according to claim 1, wherein said computing device is connected to said cooling medium inlet and holds said cooling medium inlet at a constant temperature.

6. The apparatus according to claim 1, wherein said cooling medium is water.

7. The apparatus according to claim 1, wherein:

said tank has a lid; and said cooling medium system is housed in said lid.

8. The apparatus according to claim 1, wherein said cooling medium system is divided into at least two symmetrical branches each having at least one loop.

9. The apparatus according to claim 1, further comprising:
a tank for supplying water to the liquid mixture;
a control system connected to said water-supplying tank and to said computing device for adjusting an amount of water supplied from said water-supplying tank dependent upon the water content measured by said measuring apparatus.

10. An apparatus for measuring the water content of a water-containing liquid mixture, comprising:
a tank for holding a water-containing liquid mixture having a boiling point, said tank having a top;
a heating device at said tank for controlling temperature of the liquid mixture to a temperature near the boiling point of the liquid mixture;
a cooling medium system for cooling the liquid mixture, said cooling medium system having:
a condensing surface to condense water evaporating from the liquid mixture in said tank; and
a cooling medium inlet and a cooling medium outlet, said cooling medium system being disposed at said top of said tank and conveying a cooling medium;
a temperature measurement system connected to said cooling medium system for determining a temperature difference between said cooling medium inlet and said cooling medium outlet; and
a computing device connected to said temperature measurement system for calculating the water content of the liquid mixture from said temperature difference.

11. The apparatus according to claim 10, wherein the liquid mixture is an acid/water system.

12. The apparatus according to claim 11, wherein the acid of the acid/water system is phosphoric acid.

13. The apparatus according to claim 10, wherein said cooling medium inlet is held at a constant temperature.

14. The apparatus according to claim 10, wherein said computing device is connected to said cooling medium inlet and holds said cooling medium inlet at a constant temperature.

15. The apparatus according to claim 10, wherein said cooling medium is water.

16. The apparatus according to claim 10, wherein:
said tank has a lid; and
said cooling medium system is housed in said lid.

17. The apparatus according to claim 10, wherein said cooling medium system is divided into at least two symmetrical branches each having at least one loop.

18. The apparatus according to claim 10, further comprising:
a tank for supplying water to the liquid mixture;
a control system connected to said water-supplying tank and to said computing device for adjusting an amount of water supplied from said water-supplying tank dependent upon the water content measured by said measuring apparatus.

19. A method for measuring water content of a water-containing liquid mixture having a boiling point, which comprises:
providing the liquid mixture in a tank;
disposing a cooling medium system at a top of the tank for cooling the liquid mixture, the cooling medium system having:
a condensing surface to condense water evaporating from the liquid mixture in the tank; and
a cooling medium inlet; and
a cooling medium outlet;
controlling a temperature of the liquid mixture to a temperature near the boiling point of the liquid mixture;
determining a temperature difference between the cooling medium inlet and the cooling medium outlet; and
calculating the water content of the liquid mixture from the temperature difference.

20. The method according to claim 19, which further comprises adjusting an amount of water supplied from a water supply tank dependent upon the calculated water content.

21. A method for measuring water content of a water-containing liquid mixture having a boiling point, which comprises:
disposing a cooling medium system at a top of a tank containing the liquid mixture for cooling the liquid mixture, the cooling medium system having:
a condensing surface to condense water evaporating from the liquid mixture in the tank; and
a cooling medium inlet; and
a cooling medium outlet;
controlling a temperature of the liquid mixture to a temperature near the boiling point of the liquid mixture;
determining a temperature difference between the cooling medium inlet and the cooling medium outlet; and
calculating the water content of the liquid mixture from the temperature difference.

22. The method according to claim 21, which further comprises adjusting an amount of water supplied from a water supply tank dependent upon the calculated water content.

23. The apparatus according to claim 18, wherein said control system increases an amount of water supplied from said water-supplying tank to said tank holding the liquid mixture when said temperature difference decreases.

24. The apparatus according to claim 18, wherein said control system decreases an amount of water supplied from said water-supplying tank to said tank holding the liquid mixture when said temperature difference increases.

25. The apparatus according to claim 18, wherein said control system has a processor programmed to increase an amount of water supplied from said water-supplying tank to said tank holding the liquid mixture when said temperature difference decreases.

26. The apparatus according to claim 18, wherein said control system has a processor programmed to decrease an amount of water supplied from said water-supplying tank to said tank holding the liquid mixture when said temperature difference increases.

* * * * *